United States Patent [19]

Levek et al.

[11] 4,160,112
[45] Jul. 3, 1979

[54] PROCESS FOR THE ISOLATION OF PENTABROMOPHENOL

[75] Inventors: Robert P. Levek; Rastko I. Mamuzic; John L. Sands, all of West Lafayette, Ind.

[73] Assignee: Great Lakes Chemical Corporation, West Lafayette, Ind.

[21] Appl. No.: 877,189

[22] Filed: Feb. 13, 1978

[51] Int. Cl.$^2$ ...................... C07C 37/38; C07C 39/24
[52] U.S. Cl. .................................... 568/755; 568/776
[58] Field of Search ............................. 568/755, 776

[56] References Cited

U.S. PATENT DOCUMENTS 3,051,761  8/1962  MacBeth ............................. 568/755
3,839,463 10/1974  Cohn ................................... 568/755

Primary Examiner—Werren B. Lone
Attorney, Agent, or Firm—Kirkland & Ellis

[57] ABSTRACT

A process for isolating crude pentabromophenol containing occluded bromine and hydrogen bromide as impurities comprising the steps of contacting the crude pentabromophenol with a strong acid such as hydrobromic acid, sulfuric acid, hydrochloric acid and phosphoric acid; heating the mixture in order to remove excess bromine; and recovering of the pentabromophenol, whereby formation of carbonyl-group-containing impurities during isolation is minimized.

10 Claims, No Drawings

PROCESS FOR THE ISOLATION OF PENTABROMOPHENOL

BACKGROUND OF THE INVENTION

1. Field of the Invention

This invention relates to the isolation of pentabromophenol and more particularly to a process for isolating pentabromophenol containing residual free bromine and by-product hydrogen bromide which avoids the formation of substantial quantities of undesirable impurities.

2. Description of the Prior Art

Numerous processes may be employed for replacing all the nuclear hydrogen atoms in aromatic compounds such as benzene, phenol and the like. Perbromination processes in general have involved use of up to about 20% excess bromine in the presence of various kinds of reaction media and solvents depending on the particular aromatic compound to be brominated.

Alternatively, nuclear perbrominated non-condensed aromatic compounds may be preferably obtained by reacting such a compound in the presence of a substantial excess of bromine as both reactant and the sole reaction medium. This bromination in bromine reaction takes place in the presence of a small but catalytic amount of a bromination catalyst which may include iron and aluminum, their halides, and compounds which form iron or aluminum bromide under the conditions of the reaction.

Regardless of the preparation process utilized there is obtained a perbrominated compound containing undesirable large amounts of occluded free bromine and by-product hydrogen bromide.

High levels of purity are often required for perbrominated aromatic compounds such as pentabromophenol which have found utility as flame retardant agents. In particular, it is important that such brominated products have extremely low levels of residual impurities such as free bromine, bromine-containing derivatives and the like since the presence of such impurities can have undesirable effects on the compositions in which such compounds are used as either flame retardant agents or for other purposes. Purity is particularly important from the standpoint of color and thermal stability under the processing conditions to which such compounds are subjected.

The isolation of perbrominated products obtained from the bromination in bromine reaction has been attempted by a variety of work-up procedures.

The crude reaction mixture which may contain the brominated products, excess bromine, hydrogen bromide, and catalyst can, for instance, be subjected to stripping either at atmospheric pressure or preferably under reduced pressure at about 80° C. to the point of constant weight of the residue. The crude product which is thus isolated may be further purified, for instance, by digestion with methanol, ethylene dibromide, or dilute hydrochloric acid. This method has the disadvantage that it may leave residual metal-containing catalyst in the product and is impractical on anything other than a laboratory scale.

It is also possible to replace the excess bromine in the reaction mixture by ethylene dibromide followed by filtration. The crude product can then be further purified by digestion procedures as described above. However, the substitution of excess bromine with ethylene dibromide is inconvenient because the two distill together and the resulting volume of distillate containing bromine and ethylene dibromide can be more than twice as large as the volume of excess bromine used. Furthermore, this isolation seals in the residual metal-containing catalyst, and the catalyst remains in the product even after digestion in methanol.

In a preferred variation of the isolation step it is also possible to isolate the perbromination product by replacing the excess bromine in the reaction mixture with water while distilling off the excess bromine to yield a water slurry of perbrominated product. This is then followed by filtration, washing and drying of the aqueous reaction mixture. The crude product obtained may then be purified by relatively simple digestion procedures as described above.

However, when applied to the isolation of pentabromophenol, the removal of excess bromine by transferring the reaction mixture into contact with water results in the formation of substantial quantities of the carbonyl impurities 1, 2, 4, 5, 6, 6-hexabromo-1, 4-cyclohexadien-3-one, and 1, 2, 4, 4, 5, 6-hexabromo-1, 5-cyclohexadien-3-one (hereinafter referred to as "carbonyl impurities" or "carbonyl-group-containing impurities"). The resulting pentabromophenol containing carbonyl impurities has a large melting point range and coloration ranging from orange to dark orange and is therefore not a suitable final product.

Another scheme which has been utilized in the isolation and purification of perbrominated compounds includes the steps of an immediate initial filtration of the reaction mixture followed by washing the product one or more times with methanol to give a purified product. This isolation procedure has many advantages including simplicity. However, when applied to pentabromophenol the final product also contains the undesirable carbonyl impurities. Apparently, the carbonyl impurities are formed when the crude product, containing some free bromine, comes in contact with methanol during the washing step.

Accordingly, it is a primary object of this invention to obtain a process for the isolation of pentabromophenol that is superior to the techniques that heretofore have been employed.

Another object is to provide a process for producing purified pentabromophenol which avoids the formation of undesirable impurities during isolation.

A still further object is to provide a method of the character described that may be economically employed in isolating pentabromophenol.

SUMMARY OF THE INVENTION

The foregoing and other objects, advantages, and features of the present invention may be achieved with a process for the isolation of pentabromophenol comprising the steps of contacting the crude pentabromophenol with a strong acid; heating the mixture in order to remove the excess bromine; and recovering the pentabromophenol, whereby the formation of carbonyl-group-containing impurities is minimized.

More particularly, it has been found that the acid may be selected from the group consisting of hydrobromic acid, sulfuric acid, hydrochloric acid, and phosphoric acid. Still further, it has been found that the strong acid should be at least a 2 normal solution and preferably about a 5–12 normal solution.

In addition, it has been found that the foregoing procedure is especially effective when employed with pentabromophenol obtained by perbromination in an excess of bromine without other reaction solvents being present and in the presence of a bromination catalyst.

DETAILED DESCRIPTION OF THE PREFERRED EMBODIMENTS

Unpurified, crude pentabromophenol produced by perbromination in the presence of a substantial excess of bromine acting as both reactant and the sole reacting medium and in the presence of a bromination catalyst typically contains some occluded free bromine and by-product hydrogen bromide, but otherwise has an inherent high assay and small melting point range. However, high levels of purity are often required for perbrominated aromatic compounds such as pentabromophenol. Purity is particularly important from the standpoint of color and thermal stability under the processing conditions to which pentabromophenol is often subjected.

A number of isolation and purification procedures have been applied to perbrominated aromatic compounds. However, these procedures are either uneconomical, impractical, or result in the formation of the undesirable carbonyl-group-containing impurities. This resulting pentabromophenol containing carbonyl impurities has a large melting point range and a coloration ranging from orange to dark orange and is not a suitable final product.

Typically, the perbromination of pentabromophenol in bromine occurs in the presence of a substantial excess (150% to 200%) of bromine. The bromine is placed in a flask fitted with mechanical stirrer, addition funnel with pressure equalizing side arm, thermometer and condenser. The vent from the condenser leads to a water trap which is used to collect evolved hydrogen bromide.

The reaction preferably takes place in the presence of a small but catalytic amount of a bromination catalyst such as iron powder. The iron powder is present in an amount consisting of about approximately 1 to 2 percent weight on weight of phenol. The iron catalyst is added to the bromine and the mixture is stirred while warming the mixture to the desired reaction temperature.

Phenol is then added slowly to the mixture. After complete addition, the mixture is heated and maintained at reflux (approximately 60° C.) until hydrogen bromide evolution ceases.

In accordance with this invention, it has been found that such crude pentabromophenol may be readily isolated with assurance by contacting the crude reaction mixture with a strong acid. The acid may be selected from the group consisting of hydrobromic acid, sulfuric acid, hydrochloric acid and phosphoric acid. The strong acid should be at least a 2 normal solution and preferably about a 5-12 normal solution.

The mixture is then heated in order to remove the excess bromine. The mixture can be heated to a temperature of about 40°-160° C. and preferably to a temperature of about 60°-130° C. to remove the bromine.

The recovery of the pentabromophenol may be accomplished by filtration, washing and drying either in air or in a forced air oven in order to obtain the final product.

The following examples are presented as illustrative only of the process of the invention and in no way are intended to limit the invention as to the specific features of the process described.

EXAMPLE I

Bromine, 1997.9 g (12.5 mole, 150% excess) was charged into a 1 liter 4-necked flask fitted with mechanical stirrer, addition funnel with pressure equalizing side arm, thermometer, and condenser. The vent from the condenser led to a water trap which was used to collect evolved hydrogen bromide. Iron powder, 0.94 g (1% w/w on phenol), was added to the bromine and the mixture stirred 15 minutes at room temperature. Phenol, 94.1 g (1.0 mole), was then added dropwise without heating the reaction flask. The reaction mixture was then heated and maintained at reflux (approximately 60° C.) until hydrogen bromide evolution ceased.

After cooling the reaction mixture to room temperature (25° C.), the mixture was treated with the slow addition of 250 ml of 48% aqueous hydrobromic acid while keeping the flask in a static water bath. Bromine was then distilled out and the distilled bromine was replaced with an additional 260 ml of 48% aqueous hydrobromic acid. The product was then filtered, washed with water and dried in air.

The product yield was 98.4% of theoretical on phenol, was light cream colored and had a melting point range of 230° to 232° C. The infra-red assay for the presence of the carbonyl-group was negative.

EXAMPLE II

Bromine, 1198.7 g (7.5 mole, 150% excess) was charged into the apparatus of Example I. Iron powder, 0.57 g (1% w/w on phenol), was added to the bromine and the mixture stirred 15 minutes. Phenol, 56.7 g (0.6 mole), was then added dropwise without heating the reaction flask. The reaction mixture was then heated and maintained at reflux (approximately 60° C.) until hydrogen bromide evolution ceased.

After cooling the reaction mixture to room temperature (25° C.), the mixture was treated with the slow addition of 150 ml of 24% aqueous hydrobromic acid while keeping the flask in a static water bath. Bromine was then distilled out and the distilled bromine was replaced with an additional 178 ml of 24% aqueous hydrobromic acid. The product was then filtered, washed with water and dried in air.

The product yield was 98.9% of theoretical phenol, was dark cream colored and had a melting point range of 229° to 231° C. The infra-red assay for the presence of the carbonyl-group was negative.

EXAMPLE III

The procedure of Example II was repeated except that after cooling to room temperature the mixture was treated with 150 ml of 12% aqueous hydrobromic acid. The distilled bromine was replaced with an additional 190 ml of 12% aqueous hydrobromic acid.

The product yield was 99.1% of theoretical on phenol, was light peach in color and had a melting point range of 231° to 233° C. The infra-red assay for the presence of the carbonyl-group was negative.

EXAMPLE IV

Bromine, 800 g (5.0 mole, 150% excess) was charged into a 500 ml 4-necked flask fitted as in Example I. Iron powder, 0.75 g (2% w/w on phenol), was added to the bromine and the mixture stirred at room temperature. Phenol, 37.6 g (0.4 mole), was then added dropwise without heating the reaction flask. The reaction mixture was then heated and maintained at reflux (approximately 60° C.) until hydrogen bromide evolution ceased.

After cooling the reaction mixture to room temperature (25° C.), the mixture was treated with the slow addition of 300 ml of 34% aqueous sulfuric acid while keeping the flask in a static water bath. Bromine was then distilled out until a pot temperature of 105° C. was obtained and distilled bromine was replaced with an additional 150 ml of 34% aqueous sulfuric acid. The product was then filtered, washed with water and dried in a forced air oven at 100° C.

The product yield was 97.0% of theoretical on phenol, was light tan colored and had a melting point range of 229.5° to 233° C. The infra-red assay for the presence of the carbonyl-group was negative.

EXAMPLE V

Bromine, 960 g (6 mole, 200% excess) was charged into the apparatus of Example IV. Iron powder, 0.375 g (1% w/w on phenol), was added to the bromine and the mixture stirred 15 minutes while warming to approximately 35°–40° C. Phenol, 37.6 g (0.4 mole) was then added dropwise while maintaining the temperature at 35°–40° C. The reaction mixture was then heated and maintained at reflux (approximately 60° C.) until hydrogen bromide evolution ceased.

After cooling the reaction mixture to room temperature (25° C.), the mixture was treated with the slow addition of 300 ml of 28% aqueous hydrochloric acid while keeping the flask in a static water bath. Bromine was then distilled out until a pot temperature of 105° C. was obtained. The product was then filtered, washed with water and dried in a forced air oven at 100° C.

The product yield was 97.9% of theoretical on phenol, was very light orange colored and had a melting point range of 230° to 233° C. The infra-red assay for the presence of the carbonyl-group was negative.

EXAMPLE VI

The procedure of Example V was repeated except that after cooling to room temperature the mixture was treated with 300 ml of 14% aqueous hydrochloric acid.

The product yield was 97.2% of theoretical on phenol, was light orange in color and had a melting point range of 229° to 232.5° C. The infra-red assay for the presence of the carbonyl-group was negative.

EXAMPLE VII

The procedure of Example V was repeated except that after cooling to room temperature the mixture was treated with 300 ml of 7% aqueous hydrochloric acid.

The product yield was 96.9% of theoretical on phenol, was gold orange in color and had a melting point range of 228° to 232° C. The infra-red assay for the presence of the carbonyl-group showed that a trace was present.

EXAMPLE VIII

The following example demonstrates that crude pentabromophenol may be added to the acid solution, rather than vice versa, without effect on the final pentabromophenol product. Also, the following example demonstrates that the pentabromophenol can be added to the acid solution without prior cooling to room temperature.

Bromine, 1198.7 g (7.5 mole, 150% excess) was charged into the apparatus of Example I. Iron powder, 0.57 g (1% w/w on phenol), was added to the bromine and the mixture stirred 15 minutes while warming to approximately 45°–47° C. Phenol, 56.7 g (0.6 mole), was then added dropwise while maintaining the reaction temperature at approximately 45° C. The reaction mixture was then heated and maintained at reflux (approximately 60° C.) until hydrogen bromide evolution ceased.

After cooling the reaction mixture to a pot temperature of approximately 50° C. it was transferred into 328 ml of 48% aqueous hydrobromic acid under efficient stirring in a 1 liter flask. The excess bromine was then distilled out by heating until a temperature of 105° C. was obtained. The product was filtered, washed with water and air dried.

The product was light cream colored and had a melting point range of 232°–234° C. The infra-red assay for the presence of the carbonyl-group was negative.

EXAMPLE IX

The following example demonstrates that bromine can be distilled from the reaction mixture at or near the reflux temperature without detrimental effect on the quality of the final pentabromophenol product.

Bromine, 1198.7 g (7.5 mole, 150% excess) was charged into a 1 liter 4-necked flask fitted with mechanical stirrer, addition funnel with pressure equalizing side arm, thermometer, and condenser. The vent from the condenser led to a water trap which was used to collect evolved hydrogen bromide. Iron powder, 0.57 g (1% w/w on phenol), was added to the bromine and the mixture stirred 15 minutes at a temperature of 22°–26° C. Phenol, 56.7 g (0.6 mole), was then added dropwise over a period of 110 minutes without heating the reaction flask. The reaction mixture was then heated and maintained at reflux (approximately 60° C.) until hydrogen bromide evolution ceased.

After cooling the reaction mixture to room temperature (25° C.), the mixture was treated with the addition of 328 ml of 48% aqueous hydrobromic acid under efficient stirring. Bromine was then distilled out by heating with the oil bath (maximum pot temperature 122° C.) and refluxing for 1 hour. The product was then filtered, washed with water and dried in air.

The product yield was 99.1% of theoretical on phenol, was cream colored and had a melting point range of 233° to 236° C. The infra-red assay for the presence of the carbonyl-group was negative.

EXPERIMENTAL EVALUATIONS

A study was conducted in order to determine the effect of various isolation and purification techniques on the quality of the final pentabromophenol product. Crude pentabromophenol was obtained from a pilot plant run utilizing perbromination in an excess of bromine without other reaction solvents being present and in the presence of a small but catalytically effective amount of a bromination catalyst consisting of iron powder.

The crude pentabromophenol reaction mixture was divided into 50–75 ml samples and various isolation procedures were performed on the samples. The removal of bromine was effectuated by either evaporation or distillation. When distillation was utilized, it was carried out in a 500 ml flask with the addition of 200 ml of water or acid solution. The pot temperature during distillation ranged from 60°–105° C.

TABLE 1

Pentabromophenol Quality as a Function of Isolation Technique

| Isolation Procedure | Melting Range* °C. | IR Assay (Carbonyl Impurities) |
|---|---|---|
| $Br_2$ allowed to evaporate off in hood. | 228.0–229.0 | None Present |
| $Br_2$ allowed to evaporate off under vacuum. | 227.6–229.0 | None Present |
| 200 ml of water was added and the $Br_2$ was distilled from reaction slurry. | 153.0–211.0 | Large carbonyl peak |
| 200 ml of 19.5% aqueous HCl (5.8 N) was added and the $Br_2$ was distilled from reaction slurry. | 228.0–229.3 | None Present |
| 200 ml of 33% aqueous HBr (5.2 N) was added and the $Br_2$ was distilled from reaction slurry. | 228.0–229.0 | None Present |
| 200 ml of 36% aqueous $H_3PO_4$ (4.5 M) was added and the $Br_2$ was distilled from reaction slurry. | 225.0–227.5 | Small carbonyl peak |
| 200 ml of 34% aqueous $H_2SO_4$ (9 N) was added and the $Br_2$ was distilled from reaction slurry. | 227.5–228.5 | None Present |

*Corrected melting point obtained from Hoover Melting Point Apparatus

Table 1 records the melting point range and the results of the infra-red assay for the pentabromophenol product obtained from the various isolation procedures. The presence of carbonyl impurities is evidenced by a positive infra-red assay and a large melting point range.

An inspection of the data presented in Table 1 reveals the poor quality of pentabromophenol obtained when the excess bromine is removed by distillation in the presence of water. In sharp contrast, when the excess bromine is removed by distillation in the presence of a strong acid, a pentabromophenol product of excellent quality is obtained.

The data in Table 1 also demonstrates the absence of carbonyl impurities when the bromine is allowed to evaporate off. However, this method of bromine removal is totally inefficient and impractical on anything other than a laboratory scale. The process is time consuming and leaves the final product in a solidified mass which cannot be handled by plant processing equipment.

Accordingly, the isolation process of the present invention is a practical and efficient process which gives a final pentabromophenol product of excellent quality and free of carbonyl impurities.

We claim:

1. A process for reducing the occurrence of carbonyl-group-containing impurities in pentabromophenol recovered from the reaction mixture of phenol with bromine comprising the steps of:
   (a) contacting the reaction mixture comprising crude pentabromophenol with at least one aqueous strong acid selected from the group consisting of hydrochloric acid, phosphoric acid, sulfuric acid, and hydrobromic acid;
   (b) applying heat to the mixture resulting from step (a) at temperature of about 40°–160° C. to remove free bromine therefrom by distillation; and
   (c) removing pentabromophenol from the mixture resulting from step (b).

2. A process as claimed in claim 1, wherein the strong acid is at least a 2 normal solution.

3. A process as claimed in claim 1, wherein heating the mixture in order to remove excess bromine comprises heating the mixture at a temperature of about 60°–130° C.

4. A process as claimed in claim 1, wherein the removing of pentabromophenol comprises the steps of filtration, washing and drying.

5. A process as claimed in claim 1, wherein the strong acid is preferably about a 5–12 normal solution.

6. In a process for preparing pentabromophenol comprising the steps of reacting phenol with an excess of bromine in the presence of a small but catalytically effective amount of a bromination catalyst to produce a reaction mixture; heating the reaction mixture to reflux temperature, and continuing heating until evolution of hydrogen bromide ceases; cooling the heated reaction mixture to about ambient temperature to obtain a cooled reaction mixture comprising crude pentabromophenol, and isolating the pentabromophenol from the resulting reaction mixture, the improvement comprising the steps of:
   (a) contacting the cooled reaction mixture comprising crude pentabromophenol with at least one aqueous strong acid selected from the group consisting of hydrochloric acid, phosphoric acid, sulfuric acid, and hydrobromic acid;
   (b) applying heat to the mixture resulting from step (a) at temperature of about 40°–160° C. to remove free bromine therefrom by distillation; and
   (c) removing pentabromophenol from the mixture resulting from step (b), whereby the occurrence of carbonyl-containing impurities in the pentabromophenol is reduced.

7. A process as claimed in claim 6, wherein the strong acid is at least a 2 normal solution.

8. A process as claimed in claim 6, wherein heating the mixture in order to remove excess bromine comprises heating the mixture at a temperature of about 60°–130° C.

9. A process as claimed in claim 6, wherein the removing of pentabromophenol comprises the steps of filtration, washing and drying.

10. A process as claimed in claim 6, wherein the strong acid is preferably about a 5–12 normal solution.

* * * * *